(12) United States Patent
Ouchi

(10) Patent No.: US 6,520,954 B2
(45) Date of Patent: Feb. 18, 2003

(54) MANIPULATING SECTION FOR AN ENDOSCOPIC TREATMENT INSTRUMENT

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 62 days.

(21) Appl. No.: 09/734,929

(22) Filed: Dec. 13, 2000

(65) Prior Publication Data
US 2001/0004676 A1 Jun. 21, 2001

(30) Foreign Application Priority Data
Dec. 14, 1999 (JP) .......................... 11-353838
Dec. 15, 1999 (JP) .......................... 11-355304

(51) Int. Cl.⁷ .............................. A61B 17/00
(52) U.S. Cl. ................... 606/1; 604/104; 604/106
(58) Field of Search ................ 606/1; 600/106, 600/104

(56) References Cited
U.S. PATENT DOCUMENTS 5,487,392 A  1/1996  Haaga
5,601,533 A  2/1997  Hancke et al.
5,718,237 A  2/1998  Haaga
5,993,470 A * 11/1999  Yoon ........................... 606/185
6,110,127 A * 8/2000  Suzuki ........................ 600/565
2001/0005778 A1 * 6/2001  Ouchi ......................... 600/564

FOREIGN PATENT DOCUMENTS

JP  9-103433  4/1997
JP  10216134  8/1998

* cited by examiner

Primary Examiner—Denise L. Esquivel
Assistant Examiner—Marc Norman
(74) Attorney, Agent, or Firm—Greenblum & Bernstein, P.L.C.

(57) ABSTRACT

A manipulating section for an endoscopic treatment instrument a frame plate adapted to be fixed to or disengaged from an entrance of a treatment instrument insertion channel in an endoscope, an outer sheath lock nut by which a basal end portion of an outer sheath can be moved back and forth on an elongation of an axis of the entrance of the treatment instrument insertion channel along the frame plate or fixed, and an elongating member lock nut by which a basal end portion of an elongating member can be moved back and forth on the elongation of the axis of the entrance of the treatment instrument insertion channel along the frame plate or fixed.

17 Claims, 15 Drawing Sheets

FIG. 5
FIG. 6
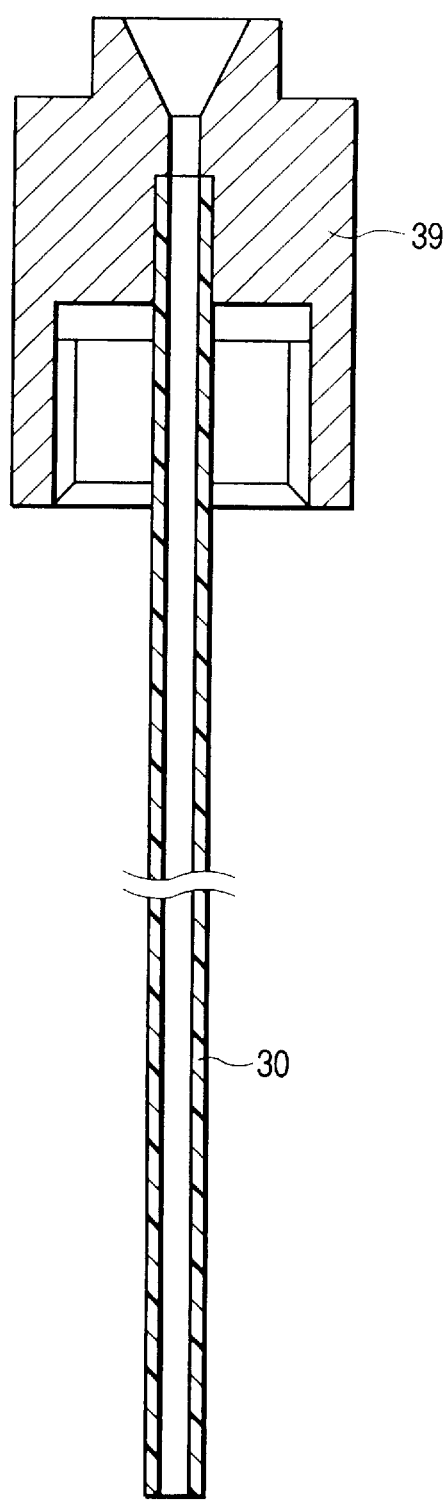
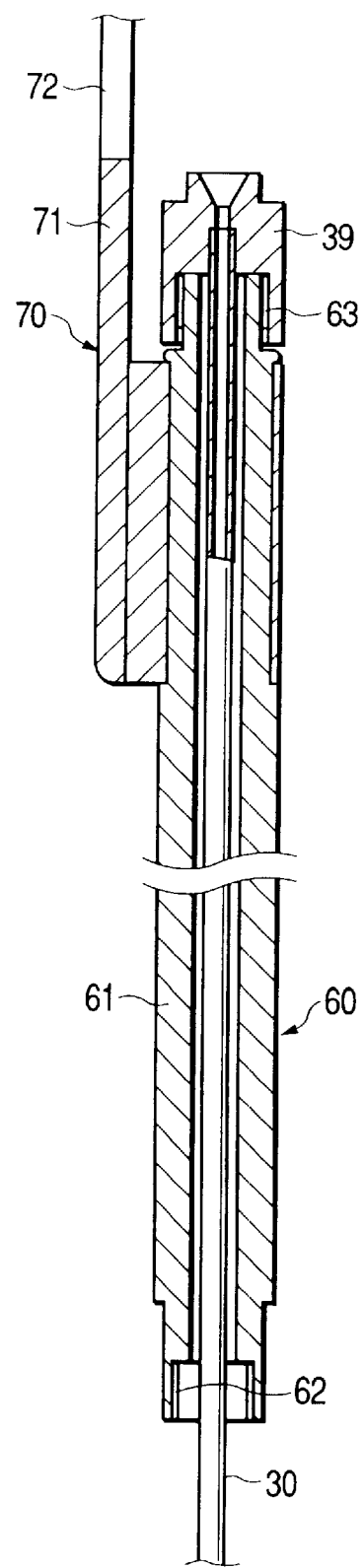

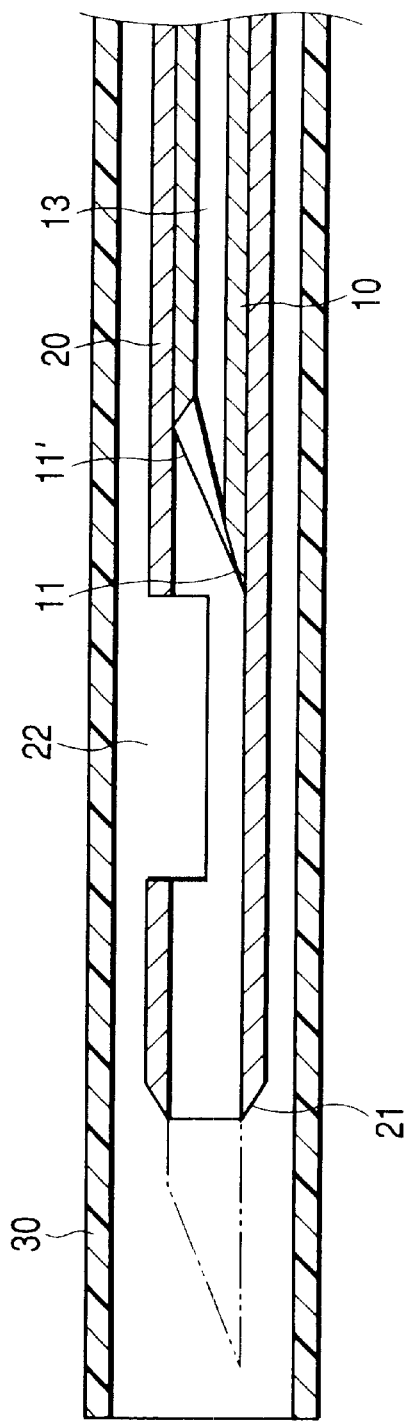
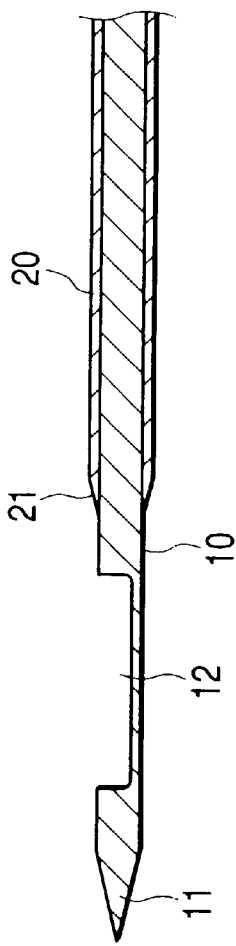

MANIPULATING SECTION FOR AN ENDOSCOPIC TREATMENT INSTRUMENT

BACKGROUND OF THE INVENTION

The present invention relates to a manipulating section for an endoscopic treatment instrument including a hollow, first member, and a second member inserted into and movable relative to the first hollow member.

A Menghini tissue collecting needle, which is used for a biopsy of the pancreas, the liver and other organ by being inserted into and removed from a treatment instrument insertion channel in an endoscope, is known as one of endoscopic treatment instruments.

FIG. 17 shows the distal end portion of the Menghini tissue collecting needle which comprises a rod-shaped needle shaft 10 having a pointed end 11 and a tissue retaining recess 12 formed in the lateral side of an area close to the needle end 11 and into which an excised tissue specimen is retained.

A cannula or outer sheath 20 is fitted over the needle shaft 10 to be capable of moving back and forth along the longitudinal axis and it has an annular blade 21 formed on the inner circumference of the tip for cutting off the tissue retained in the recess 12.

The Menghini tissue collecting needle is simply a combination of a needle shaft and a outer sheath and used after being passed into a rigid endoscope.

If the Menghini needle is to be used by passage through a treatment instrument insertion channel in a so-called "soft endoscope" having a flexible insertion portion, an extremely great frictional resistance is caused within the tortuous treatment instrument insertion channel, making it difficult to manipulate the needle shaft and the outer sheath so they can be moved back and forth by small amounts and independently of each other. Consequently, it has been impossible to collect a tissue specimen in a safe and rapid manner.

Japanese Patent Kokai Publication No. Hei. 9-103433 discloses another endoscopic treatment instrument having a hollow, outer sheath (19), a hollow piecing needle (20) inserted into the outer sheath, and a stylette or metal core (21) inserted into the piecing needle. In this instrument, a piecing section sliding section (10) of the outer sheath (19) can be fixed with respect to a piecing manipulating section (9) using a knob (15), the piecing needle (20) can not be fixed with respect to the manipulating section (9). Further, since the stylette (21) is fixed with respect to the piecing needle (20), the stylette (21) cannot be moved independently during endoscopic treatment.

That is, the outer sheath (19), the piecing needle (20) and the stylette (21) can not be moved independently of one another during endoscopic treatment.

This is very inconvenient. For example, if the outer sheath (19) is moved slightly forward or backward by loosing the knob (15) and moving the sliding section (10) of the outer sheath (19), the piecing needle (20) is also moved to undesirably be pieced into or removed from a mucosa layer. That is, the outer sheath (19) can not be moved while keeping the piecing needle (2) stationary.

This inconvenience is also encountered during endoscopic treatment with a high frequency instrument. A doctor wants to move an outer sheath alone while keeping a snare wire stationary during surgery for removing a polyp, but cannot do so readily with the available instrument.

SUMMARY OF THE INVENTION

An object of the present invention is to provide a manipulating section for an endoscopic treatment instrument, which can fix a hollow member and another member inserted into the hollow member independently.

Another object of the present invention to provide a manipulating section for an endoscopic treatment instrument, which can move a hollow member and another member inserted into hollow member independently.

Yet another object of the present invention to provide a manipulating section for an endoscopic treatment, which can permit movement of one of a hollow member and another member inserted into the hollow member while keeping the other stationary.

Still another object of the present invention is to provide a manipulating section for an endoscopic tissue collecting instrument that allows for safe and rapid collection of a tissue specimen irrespective of whether it is used with a rigid or soft endoscope.

Further another object of the present invention is to provide a manipulating section for an endoscopic treatment instrument in which not only an outer sheath or hollow member but also a member disposed inside the outer sheath or hollow member to be movable in the longitudinal direction can be fixed with respect to an endoscope independently of each other.

According to a first aspect of the present invention, there is provided a manipulating section for an endoscopic treatment instrument, which has the first and second holding members. The first holding member can hold an end of a hollow, first member and can be selectively fixed or movable with respect to an endoscope during use.

According to a second aspect of the present invention, a manipulating section of an endoscopic tissue collecting instrument is designed such that it can be fixed to or disengaged from the entrance of a treatment instrument insertion channel in an endoscope. The basal end portion of a needle shaft and that of an outer sheath can be moved back and forth in unison along the longitudinal axis or fixed. Either the basal end portion of the needle shaft or that of the outer sheath is adapted to be capable of moving along the longitudinal axis or being fixed relative to the other of the basal end of the outer sheath or that of the needle shaft. Because of this design, both the operation of piercing the needle tip into the tissue and that of cutting off the tissue specimen collected in the tissue retaining recess can conveniently be performed from the side closer to the operator and, hence, the manipulating section of the invention allows for safe and quick collection of a tissue specimen irrespective of whether the endoscopic tissue collecting instrument is used with a rigid or soft endoscope.

According to a third aspect of the present invention, a manipulating section for an endoscopic treatment instrument is designed such that the basal end of an outer sheath and that of a member inserted into and passed through the outer sheath can be moved back and forth or fixed independently of each other along a frame plate adapted to be fixed to or disengaged from the entrance of a treatment instrument insertion channel in an endoscope. Not only an operation for moving the member back and forth with the outer sheath be fixed, but also an operation for moving the outer sheath with the member be fixed, and operation for fixing both the outer sheath and the member can be conducted as desired, thereby enabling endoscopic treatment in a simple and speedy manner.

A manipulating section according to the present invention is preferably applied to an endoscopic treatment instrument including a hollow, first member and a second member inserted into and movable relative to the first hollow member. The manipulating section is preferably designed to have a first plate, a first holding member holding an end of the first hollow member, the first holding member being movable along the plate, and selectively fixed with respect to the plate, and a second holding member holding an end of the second member, the second retaining being movable along the plate, and selectively fixed with respect to the plate.

The manipulating section may further has a coupling section connecting the plate to a socket of an endoscope, the socket being located at an inlet of a treatment instrument insertion channel of the endoscope.

The manipulating section may further has a second plate movable along and selectively fixed with respect to the first plate, wherein the first holding member is movable along the second plate and selectively fixed onto the second plate, and the second holding member is fixed onto the second plate.

The manipulating section may further has a second plate through which the first holding member is movable along the plate, and selectively fixed with respect to the plate.

The treatment instrument, to which the manipulating section is applied, may further includes a hollow, third member such that the second member is inserted into and movable relative to the third member, and an end of the third member is fixedly coupled with respect to the plate.

The treatment instrument, to which the manipulating section is applied, may be designed such that the second member is hollow, and the treatment instrument further includes a third member inserted into and movable relative to the hollow, second member. In this case, it is preferable that the manipulating section further has a third holding member holding an end of the third member, the third holding member being movable along the plate, and selectively fixed with respect to the plate.

The treatment instrument, to which the manipulating section is applied, may be designed such that the first member includes an outer sheath, the second member includes a needle shaft, and the third member includes a guide tube.

The treatment instrument, to which the manipulating section is applied, may be designed such that the first member includes a guide tube, the second member includes an outer sheath, and the third member includes a needle shaft.

The treatment instrument, to which the manipulating section is applied, may be designed such that the first member includes an outer sheath, and the second member includes a snare wire.

The manipulating section is preferably designed such that the first holding member is located between the coupling section and the second holding member.

The present invention further provides a manipulating section for an endoscopic tissue collecting instrument having a needle shaft with a needle tip formed at a distal end thereof, and an outer sheath fitted over the needle shaft to be capable of moving back and forth along a longitudinal axis, one of the needle shaft and the outer sheath having a tissue retaining recess formed in a lateral side of an area close to the distal end and the other of the outer sheath and the needle shaft having a blade formed at the distal end to cut off a tissue retained in the recess. The manipulating section is designed such that: the manipulating section can be fixed to or disengaged from an entrance of a treatment instrument insertion channel in an endoscope; a basal end portion of the needle shaft and a basal end portion of the outer sheath can be moved back and forth in unison along the longitudinal axis or fixed; and one of the basal end portion of the needle shaft and the basal end portion of the outer sheath is adapted to be capable of moving along the longitudinal axis or being fixed relative to the other of the basal end portion of the outer sheath and the other of the needle shaft.

A slider plate may be provided in such a way that the one of the basal end portion of the needle shaft and the basal end portion of the outer sheath is engaged with the slider plate movably to be capable of moving along the longitudinal axis, and the other of the basal end portion of the outer sheath and the basal end portion of the needle shaft is fixed to the slider plate, and the slider plate is capable of moving back and forth or being fixed relative to a frame of the manipulating section.

Each of the needle shaft and the outer sheath may have flexibility.

The needle shaft and the outer sheath maybe passed through a guide tube over the entire length thereof, and a basal end of the guide tube may be brought into engagement in the manipulating section.

The present invention further provides a manipulating section for manipulating, from an operator side, an endoscopic treatment instrument having an outer sheath inserted into and passed through a treatment instrument insertion channel in an endoscope and adapted to be manipulated, from the operator side, to be moved back and forth along a longitudinal axis, and an elongating member disposed within and passed through the outer sheath, and adapted to be manipulated, from the operator side, to be moved back and forth along the longitudinal axis. The manipulating section includes: a frame plate adapted to be fixed to or disengaged from an entrance of the treatment instrument insertion channel in the endoscope; an outer sheath lock nut by which a basal end portion of the outer sheath can be moved back and forth on an elongation of an axis of the entrance of the treatment instrument insertion channel along the frame plate or fixed; and an elongating member lock nut by which a basal end portion of the elongating member can be moved back and forth on the elongation of the axis of the entrance of the treatment instrument insertion channel along the frame plate or fixed.

A guide tube may be provided, which is inserted into and passed through the treatment instrument insertion channel in the endoscope, the outer sheath being inserted into and passed through the guide tube.

The manipulating section may further include: a guide tube lock nut by which a basal end portion of the guide tube can be moved back and forth on the elongation of the axis of the entrance of the treatment instrument insertion channel along the frame plate or fixed.

The present disclosure relates to the subject matter contained in Japanese patent application Nos. Hei. 11-353838 (filed on Dec. 14, 1999), and Hei. 11-355304 (filed on Dec. 15, 2000), which are expressly incorporated herein by reference in their entireties.

BRIEF DESCRIPTION OF THE DRAWINGS

FIG. 5 shows in section a guide tube in the endoscopic tissue collecting instrument;

FIG. 6 is a longitudinal section of a coupling fixing portion of the manipulating section for the endoscopic tissue collecting instrument;

FIG. 15 shows in section the distal end portion of another endoscopic tissue collecting instrument;

FIG. 17 is a longitudinal section of the distal end portion of a conventional endoscopic tissue collecting instrument.

DESCRIPTION OF THE PREFERRED EMBODIMENT

Preferred embodiments of the invention are described below with reference to accompanying drawings.

Figure 2:
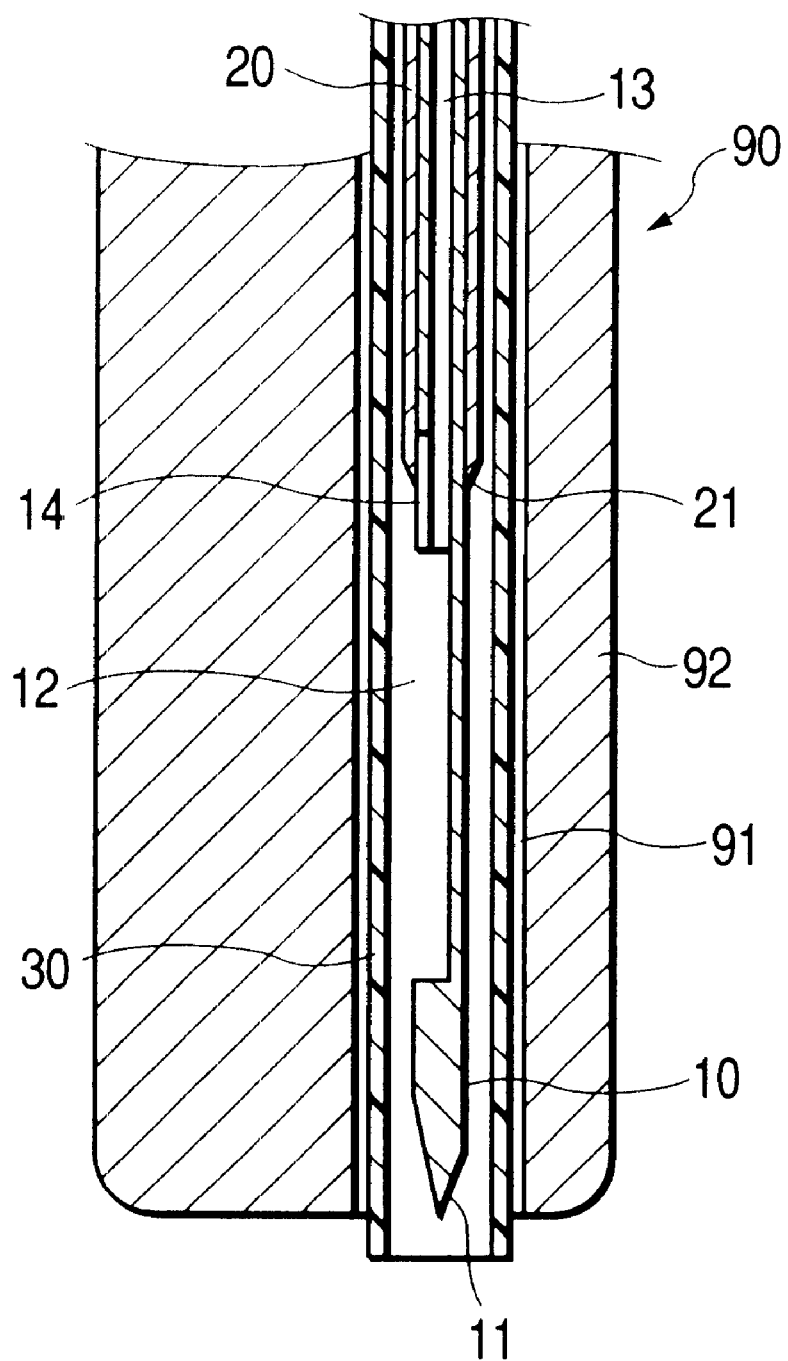
FIG. 2 shows in section the distal end portion of the endoscopic tissue collecting instrument as it has been set in an endoscope.

FIG. 2 shows a soft endoscope 90 with a treatment instrument insertion channel 91 into which an endoscopic tissue collecting instrument is passed until its distal end portion has reached an area within the distal end portion of a flexible endoscopic insertion portion 92.

The needle shaft 10 of the tissue collecting instrument has a tip 11 pointed forward and it also has a tissue retaining recess 12 formed in the lateral side of an area just behind the needle tip 11 for retaining a tissue specimen.

An aspiration channel 13 that communicates with the tissue retaining recess 12 is formed through the entire length of that part of the needle shaft 10 which is rearward of the recess 12. Hence, the part of the needle shaft 10 which is rearward of the recess 12 is in pipe form.

The needle shaft 10 also has a groove 14 that is formed adjacent an area behind the recess 12 and a rod or the like may be inserted into the groove to push out a tissue specimen collected in the recess 12. In the embodiment under discussion, the tip 11 of the needle shaft 10 has no hollow portion but, if desired, the needle shaft 10 may entirely be shaped as a pipe.

The needle shaft 10 is typically formed of a flexible plastic material. Alternatively, it may be formed of a stainless steel or other metallic material if the portion which is in pipe form is sufficiently thin-walled that it is flexible enough to be passed through a soft endoscope.

The outer sheath 20 is fitted over the needle shaft 10 so that it is capable of moving back and forth along the longitudinal axis. The distal end portion of the outer sheath 20 which is formed as a thin-walled tube is tapered such that an annular blade 21 is formed on the inner circumference of the outer sheath 20 at its distal end.

The outer sheath 20 and the needle shaft 10 are passed through a flexible guide tube 30 before they are passed through the treatment instrument insertion channel 91 of the soft endoscope 90 so that they will not have direct contact with the channel 91. The guide tube 30 may be omitted if the treatment instrument insertion channel 91 is used without the risk of being damaged by the needle tip 11 or the blade 21.

Figure 3:
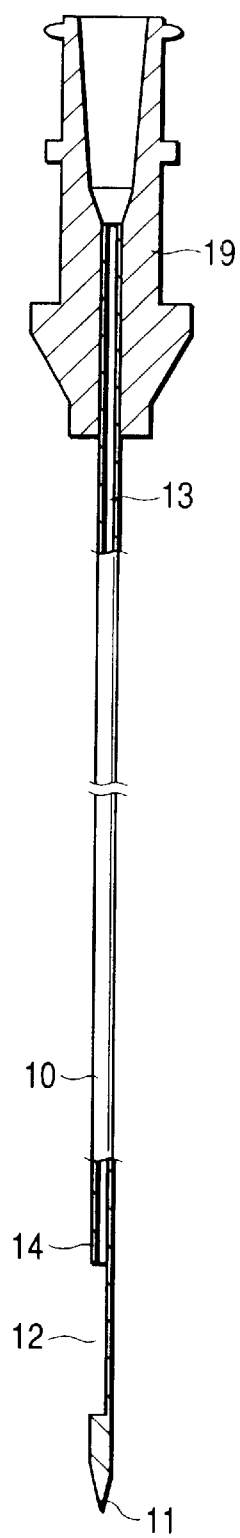
FIG. 3 shows in section the general layout of a needle shaft in the endoscopic tissue collecting instrument.
Figure 4:
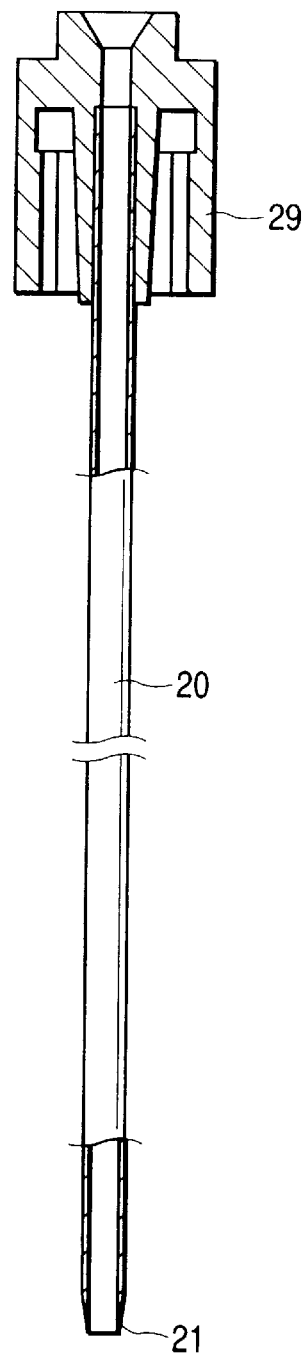
FIG. 4 shows in section the general layout of an outer sheath in the endoscopic tissue collecting instrument.

FIGS. 3, 4 and 5 show the needle shaft 10, outer sheath 20 and guide tube 30, respectively, on their own. For connection to an aspirating device, the needle shaft 10 has a socket 19 attached to the basal end portion which is typically in the form of a Luer-Lok male socket. The outer sheath 20 also has a socket 29 attached to the basal end portion which is typically in the form of a Luer-Lok female socket. The guide tube 30 also has a socket 39 attached to the basal end portion which is furnished with a female thread.

Figure 1:
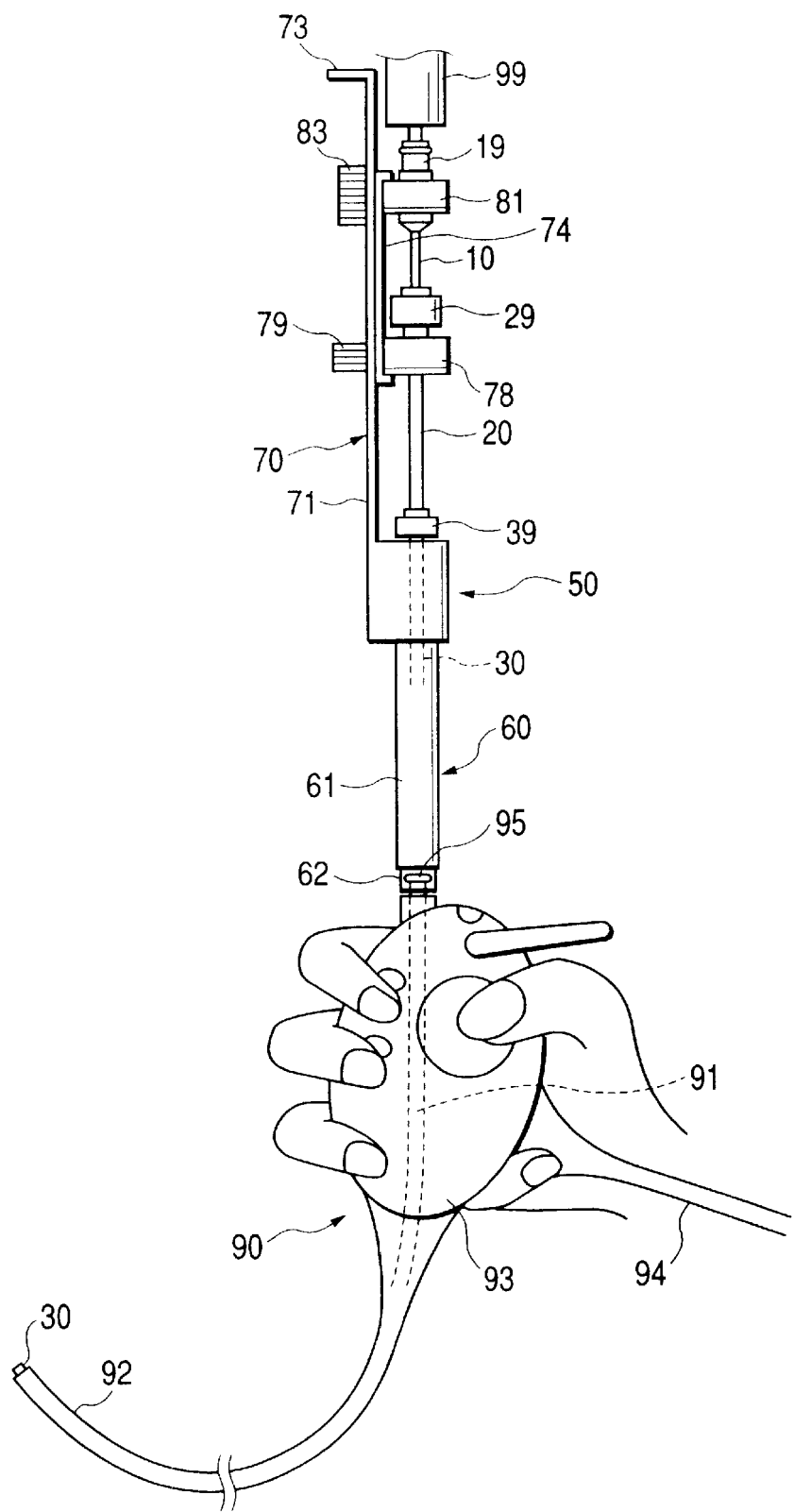
FIG. 1 is an exterior view showing how an endoscopic tissue collecting instrument is set in an endoscope.

FIG. 1 shows the endoscopic tissue collecting instrument as it is set in the soft endoscope 90. Indicated by 91 and 92 are the aforementioned treatment instrument insertion channel and endoscopic insertion portion; 93 is the endoscope manipulating section; 94 is a coupling to a video processor and light source unit; and 95 is a socket attached to project from the entrance of the channel 91 to assist in the insertion of a treatment instrument.

The manipulating section 50 of the endoscopic tissue collecting instrument is an integral combination of a coupling fixing portion 60 and a reciprocal movement manipulating portion 70. The coupling fixing portion 60 has the basal end of the guide tube 30 fixed thereto and is attached to the socket 95, and the reciprocal movement manipulating portion 70 allows the needle shaft 10 and the outer sheath 20 to be moved back and forth.

FIG. 6 shows enlarged the coupling fixing portion 60 shown in FIG. 1 but it does not show the outer sheath 20 and the needle shaft 10 that are passed through the guide tube 30. The coupling fixing portion comprises a coupling tube 61 in a straight cylindrical form which has a coupling socket 62 at an end that can be brought into or out of engagement with the socket 95 and which is typically in the form of a Luer-Lok female socket. The coupling tube 61 is attached to the socket 95 in such a way that the longitudinal axes of the two members are in alignment.

A guide tube fixing portion 63 is formed at the other end of the coupling tube 61. Since it has a male thread, the socket 39 can be brought into or out of engagement with the guide tube fixing portion 63 so that the basal end portion of the guide tube 30 as it has been passed through the treatment instrument insertion channel 91 can be fixed to the coupling tube 61. A frame plate 71 of the reciprocal movement manipulating portion 70 is coupled to that area of the coupling tube 61 which is adjacent the guide tube fixing portion 63 in either a fixed manner or in such a way that said plate is rotatable about the longitudinal axis.

Figure 7:
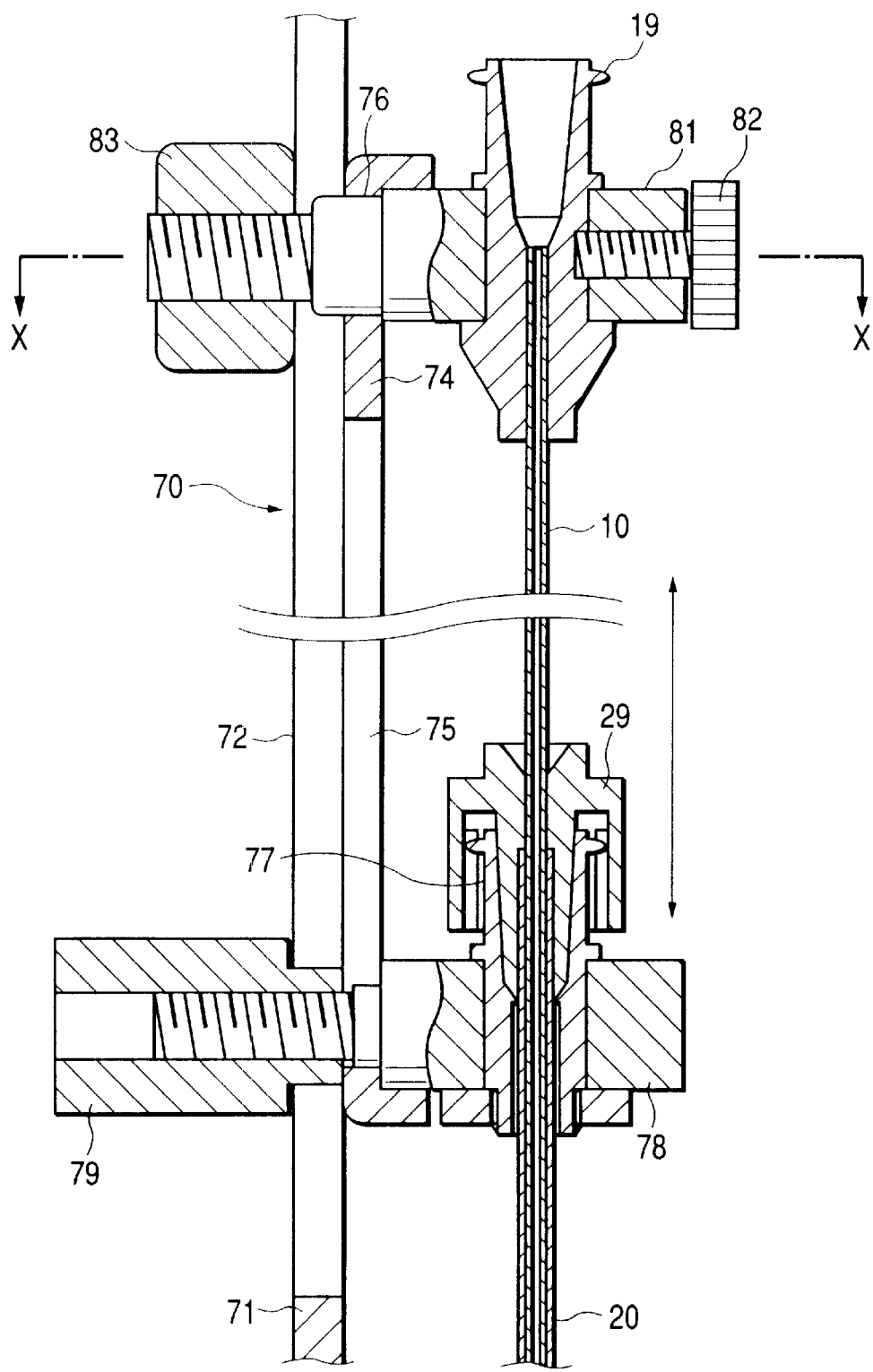
FIG. 7 is a longitudinal section of a reciprocal movement manipulating portion of the manipulating section of the endoscopic tissue collecting instrument.
Figure 8:
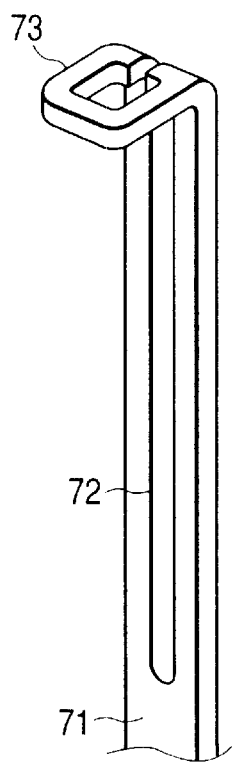
FIG. 8 is a partial perspective view of a frame plate in the endoscopic tissue collecting instrument.

FIG. 7 shows enlarged the reciprocal movement manipulating portion 70 shown in FIG. 1. As just mentioned above, the frame plate 71 is coupled to the coupling tube 61. As is also shown in FIG. 8, the frame plate 71 is a generally straight plate member having a slot 72 formed along the center line to open at the projecting end. The projecting end of the frame plate 71 is bent outward to form a stopper 73 which is to be contacted by a needle shaft lock nut 83 to be described later.

Figure 9:
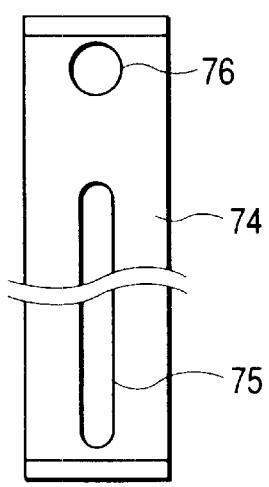
FIG. 9 is a front view of a slider plate in the endoscopic tissue collecting instrument.

As shown in FIGS. 1 and 7, a slider plate 74 made of plate member shorter than the frame plate 71 is provided in intimate contact with a surface of the frame plate 71. As shown in FIG. 9, a slot 75 with closed ends and a round hole 76 are formed in the slider plate 74 on the center line and they are spaced from each other.

Figure 10:
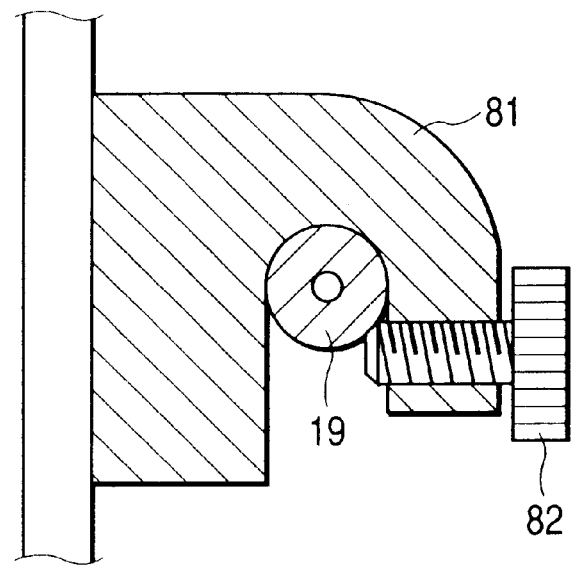
FIG. 10 is section X—X of FIG. 7 showing a needle shaft holder portion of the endoscopic tissue collecting instrument.

As shown in FIG. 7, a needle shaft holder 81 for holding the socket 19 is passed through the round hole 76 to be fixed to the slider plate 74. As is also shown in FIG. 10 which is section X—X of FIG. 7, the socket 19 is positioned in such a way that it can be brought into or out of engagement with the needle shaft holder 81 by means of a manual needle shaft fixing screw 82.

The needle shaft holder 81 has a projecting screw rod that traverses the slot 72 in the frame plate 71 and over which a manual needle shaft lock nut 83 is threaded. If the needle shaft lock nut 83 is tightened, the slider plate 74 is fixed to the frame plate 71; if the nut 83 is loosened, the slider plate 74 becomes freely movable along the slot 72.

The socket 29 can be brought into or out of engagement with a Luer-Lok male socket 77 that is an integral fixed part of an outer sheath holder 78. The outer sheath holder 78 crosses the slot 75 and has a projecting screw rod that traverses the slot 72 in the reciprocal movement manipulating portion 70 and over which a manual outer sheath lock nut 79 is threaded.

If the outer sheath lock nut 79 is tightened, the outer sheath holder 78 is fixed to the slider plate 74; if it is loosened, the outer sheath holder 78 can be moved along the slot 75 in the slider plate 74.

As a result, the outer sheath 20 moves between a state in which its distal end portion does not cover the tissue retaining recess 12 in the needle shaft 10 (see FIG. 2) and a state in which said distal end portion covers the recess completely.

The socket 19 retained by the needle shaft holder 81 and the socket 29 retained by the outer sheath holder 78 are set to satisfy such a positional relationship that they move back and forth on an extension of the longitudinal axis passed through the socket 95 and the coupling tube 61.

Given this design, the operator loosens the outer sheath lock nut 79 to move the outer sheath 20 back and forth along the longitudinal axis relative to the needle shaft 10. If the outer sheath lock nut 79 is tightened, the relative positions of the needle shaft 10 and the outer sheath 20 are fixed.

If the needle shaft lock nut 83 is loosened, the slider plate 74 becomes free to move back and forth and the needle shaft 10 and the outer sheath 20 can be moved back and forth in unison. If the needle shaft lock nut 83 is tightened, the slider plate 74 is fixed to the frame plate 71 and the needle shaft 10 is fixed to become no longer movable along the longitudinal axis (if the outer sheath lock nut 79 has also been tightened, the needle shaft 10 and the outer sheath 20 are both fixed).

Describe will be given of how a tissue specimen for biopsy is collected from the liver, the pancreas or other organ by means of the endoscopic tissue collecting instrument according to the embodiment described above.

First, as shown in FIGS. 1 and 2, the coupling socket 62 of the coupling fixing portion 60 is fixed to the socket 95. Then, the distal end of the guide tube 30 projects slightly from the distal end of the insertion portion 92 of the soft endoscope 90.

Figure 11:
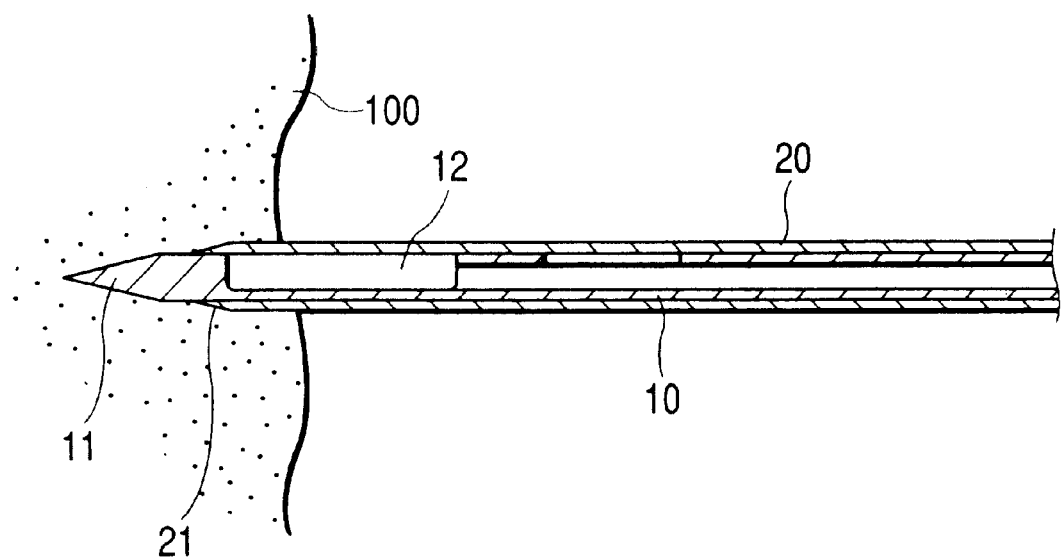
FIG. 11 is a longitudinal section showing the distal end portion of the endoscopic tissue collecting instrument as it is in the first phase of use.

With the tip 11 of the needle shaft 10 projecting slightly from the distal end of the outer sheath 20, the outer sheath lock nut 79 is tightened to make the needle shaft 10 integral with the outer sheath 20. Then, the needle shaft lock nut 83 is loosened and the slider plate 74 is pressed down, whereupon the needle tip 11 is pierced into a tissue 100 as shown in FIG. 11.

Figure 12:
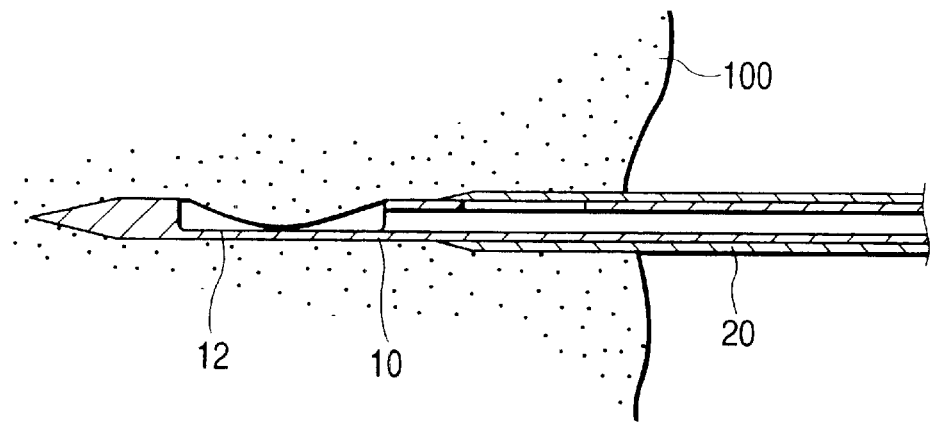
FIG. 12 is a longitudinal section showing the distal end portion of the endoscopic tissue collecting instrument as it is in the second phase of use.

When the tip 11 of the needle shaft 10 has been pierced to an appropriate depth, the needle shaft lock nut 83 is tightened, the outer sheath lock nut 79 is loosened and only the outer sheath 20 is pulled back toward the operator, whereupon the tissue retaining recess 12 becomes exposed to receive a portion of the tissue 100 as shown in FIG. 12.

Figure 13:
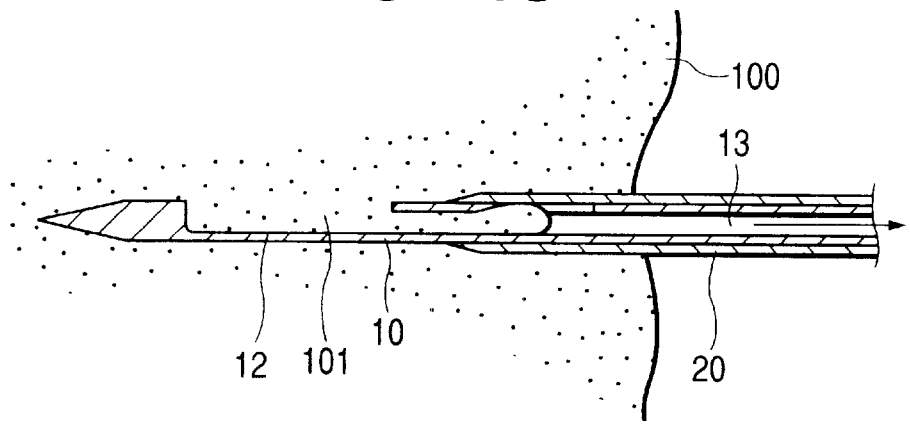
FIG. 13 is a longitudinal section showing the distal end portion of the endoscopic tissue collecting instrument as it is in the third phase of use.

Then, an aspirating device 99 connected to the socket 19 on the needle shaft 10 is activated and vacuum is drawn from the tissue retaining recess 12 via the aspiration channel 13, whereupon the tissue specimen 101 is sucked into the recess 12 and further inward to reach the area near the entrance of the aspiration channel as shown in FIG. 13.

Figure 14:
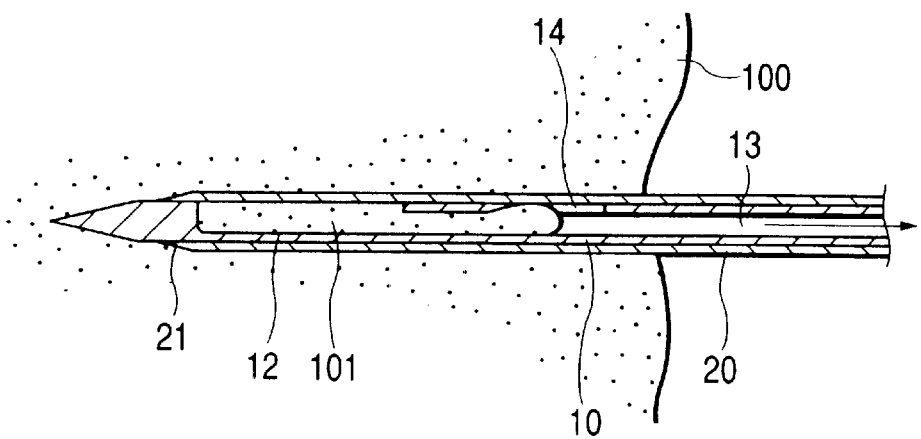
FIG. 14 is a longitudinal section showing the distal end portion of the endoscopic tissue collecting instrument as it is in the fourth phase of use.
Figure 16:
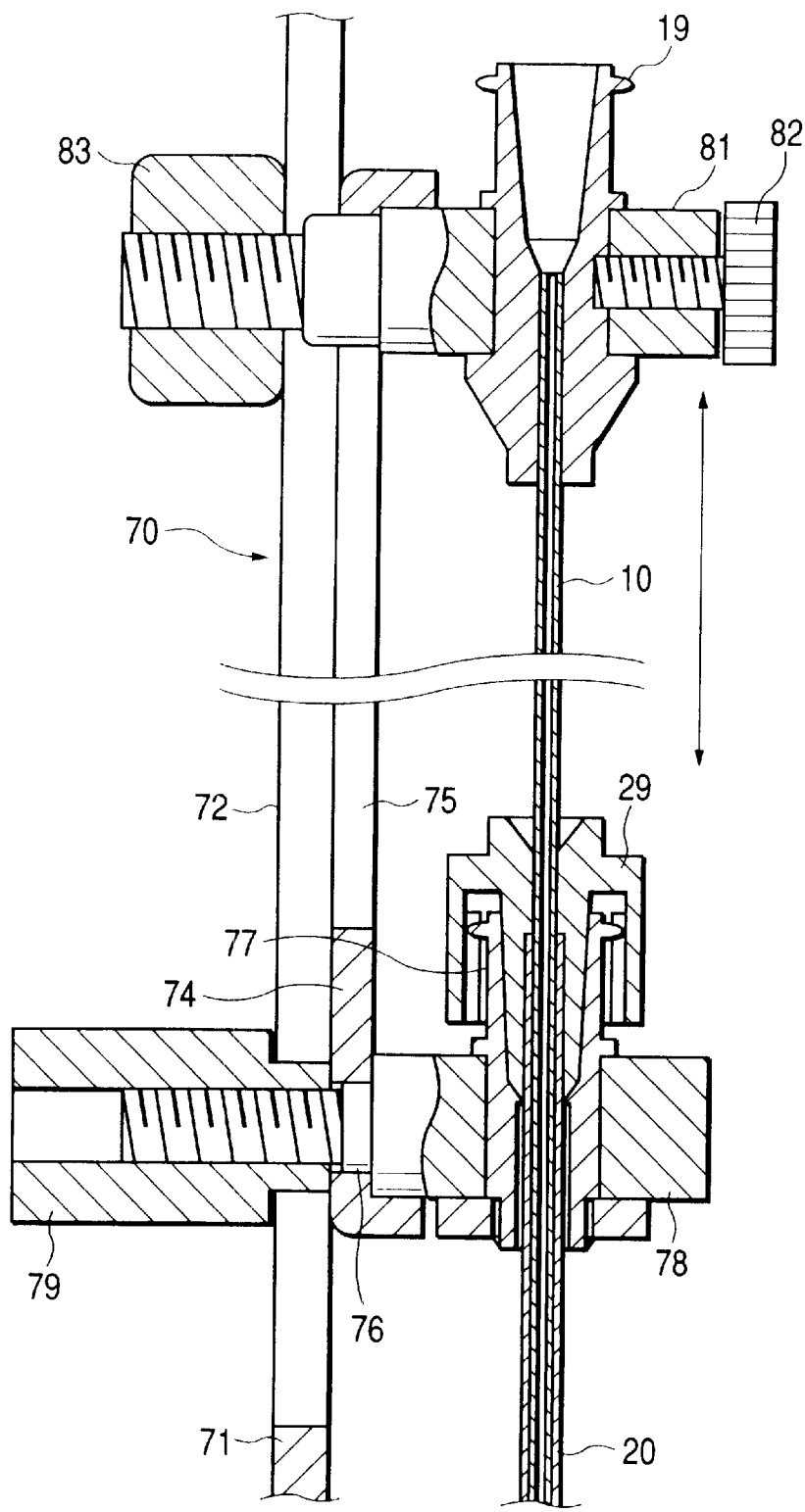
FIG. 16 is a longitudinal section of the reciprocal movement manipulating portion of the manipulating section for the endoscopic tissue collecting instrument.

As soon as this state is obtained, only the outer sheath 20 is pushed forward, whereupon the tissue specimen 101 is severed from the rest of the tissue 100 with the blade 21 of the outer sheath 20 and retained in the recess 12 as shown in FIG. 14.

Thus, both the operation for moving the needle shaft 10 and the outer sheath 20 back and forth in unison and the operation for moving only the outer sheath 20 back and forth are performed in a simple way to achieve easy collection of the tissue specimen 101.

After the collection of the tissue specimen 101, the needle shaft fixing screw 82 is loosened and the needle shaft 10 is withdrawn and a suitable device such as a fine rod is inserted into the groove 14 to push the tissue specimen 101 out of the recess 12 for recovery.

The present invention is by no means limited to the embodiment described above and various modifications can be made. For example, the tissue retaining recess 22 maybe formed in the outer sheath 20 and a blade 11' for cutting off the tissue specimen 101 may be formed on the needle shaft 10 as shown in FIG. 15. In the case of a tissue collecting instrument of this design, the slider plate 74 may be provided on opposite side so that the needle shaft holder 81 is adapted to be capable of moving back and forth, with the outer sheath holder 78 being fixed not to the frame plate 71 but to the slider plate 74.

FIGS. 18 to 23 show another embodiment of the present invention. In the previous embodiment, the socket 39 is fixedly mounted to the coupling tube 61 through the guide tube fixing portion 63, whereas in this embodiment shown in FIGS. 18 to 23, the socket 39 is movably fixed to the frame plate 71. Further, in this embodiment, the socket 29 is movably fixed to the frame plate 71 without the use of the slider plate 74.

Figure 18:
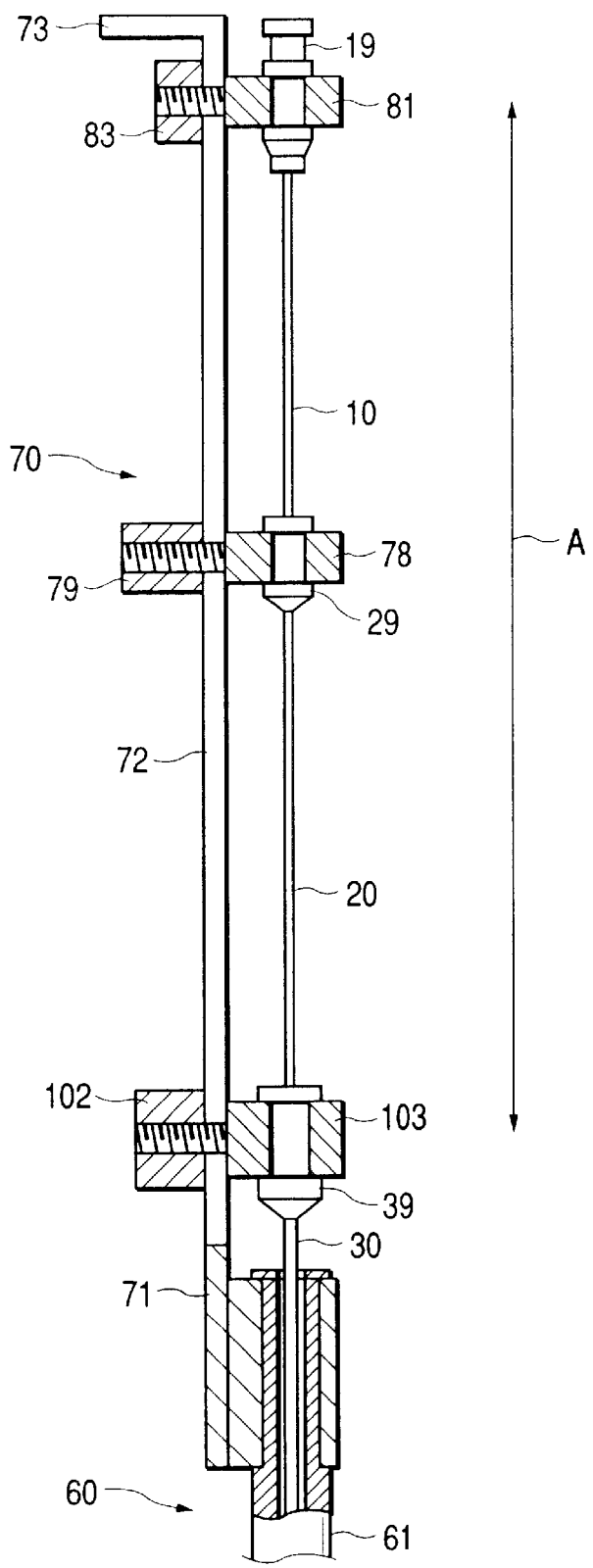
FIG. 18 is a longitudinal section of a reciprocal movement manipulating portion of another manipulating section for an endoscopic tissue collecting instrument.
Figure 19:
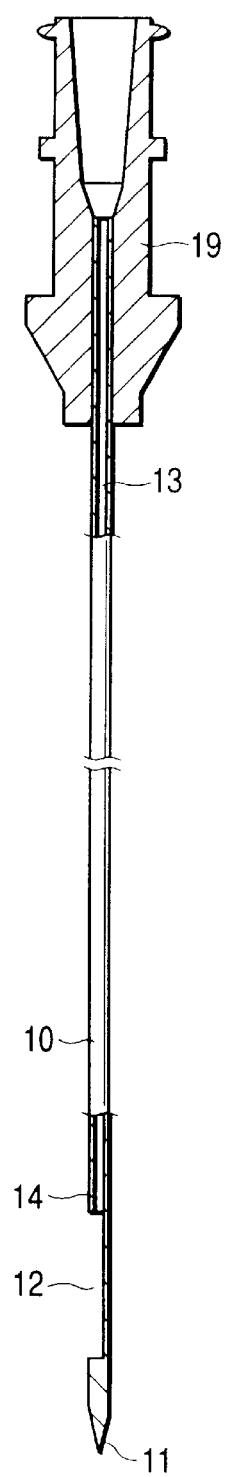
FIG. 19 shows in section the general layout of the needle shaft in the endoscopic tissue collecting instrument.
Figure 20:
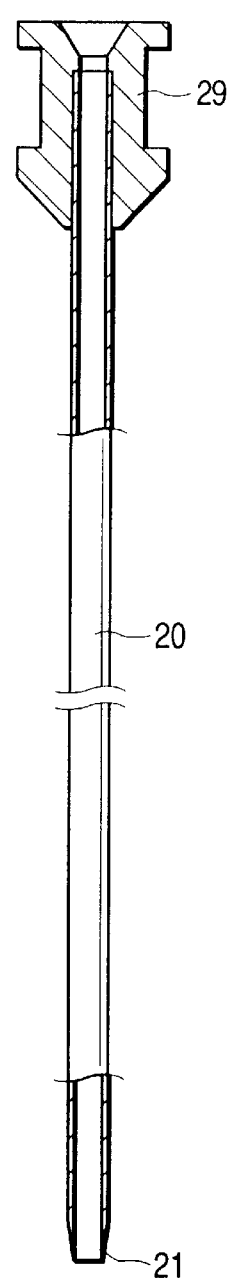
FIG. 20 shows in section the general layout of the outer sheath in the endoscopic tissue collecting instrument.
Figure 21:
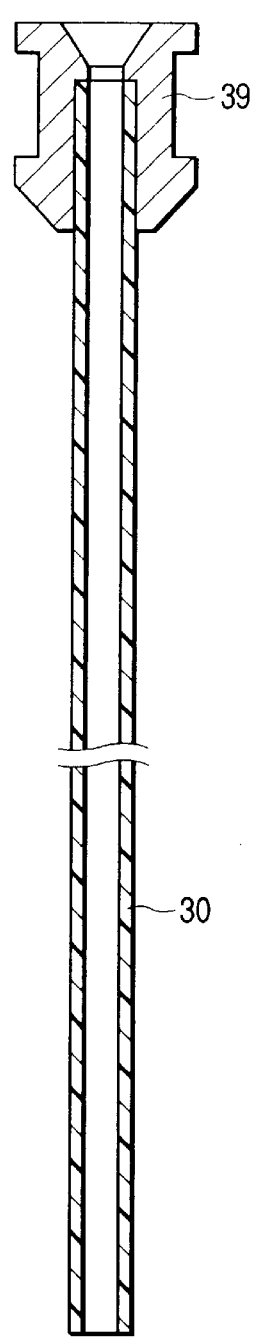
FIG. 21 shows in section the guide tube in the endoscopic tissue collecting instrument.
Figure 22:
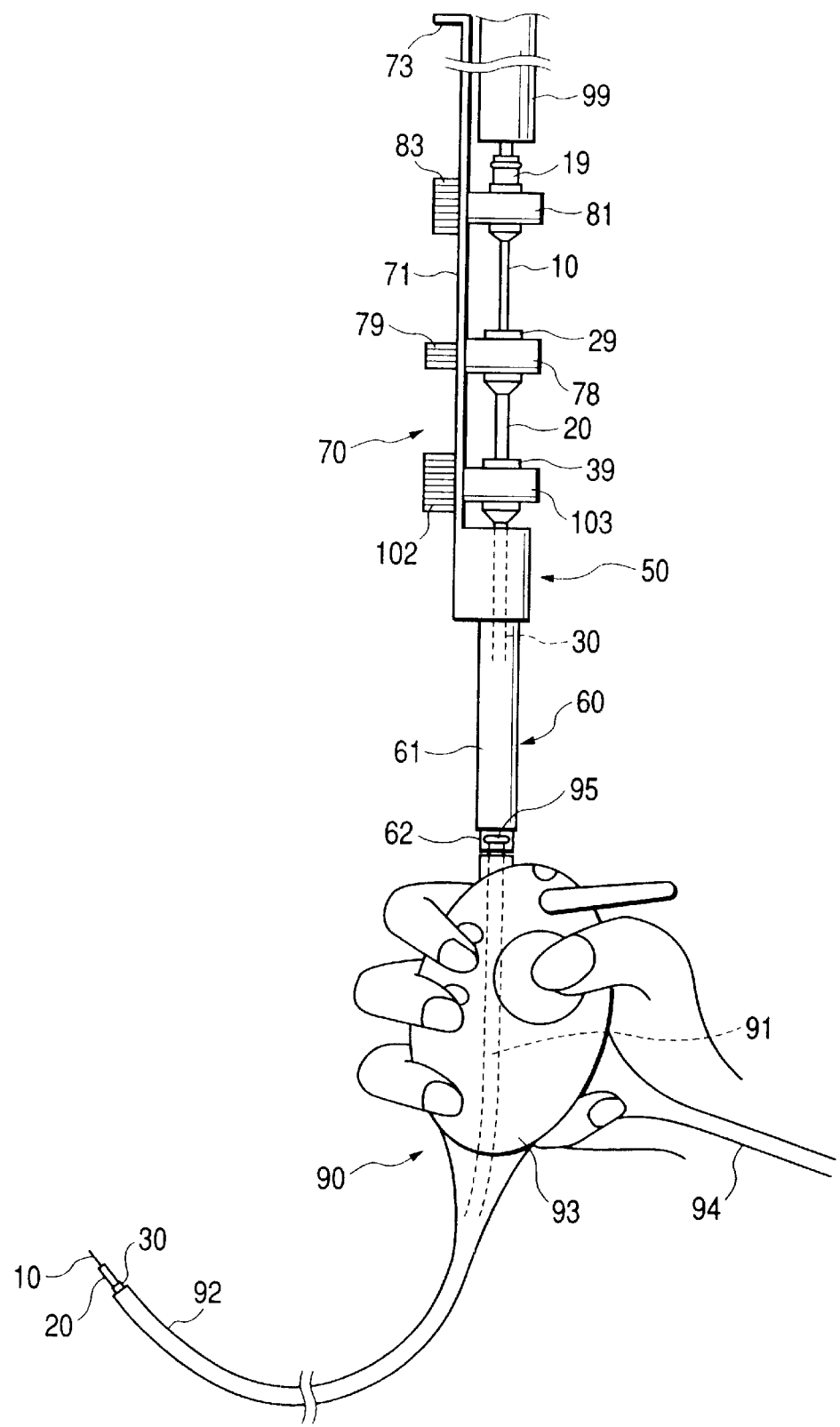
FIG. 22 is an exterior view showing how the endoscopic tissue collecting instrument is set in the endoscope.
Figure 23:
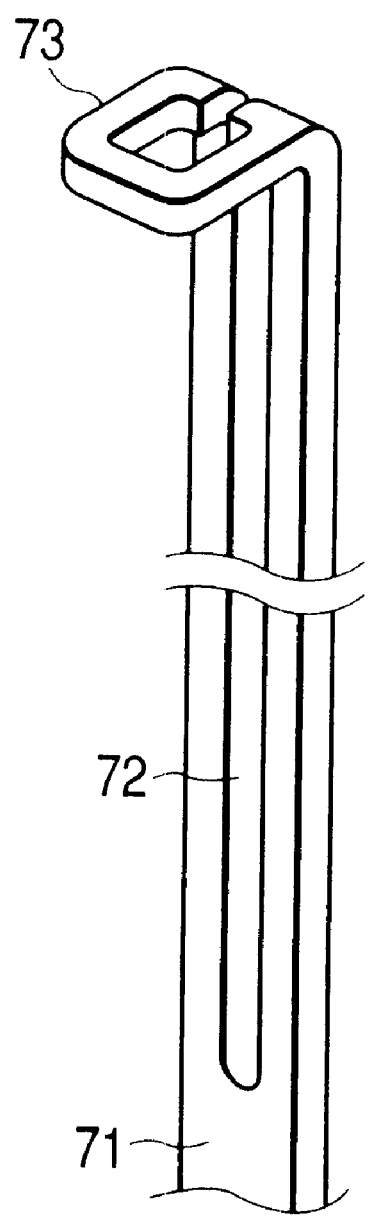
FIG. 23 is a partial perspective view of a frame plate in the endoscopic tissue collecting instrument.

FIGS. 19, 20 and 21 respectively show the needle shaft 10, outer sheath 20 and guide tube 30 on their own, and FIG. 18 shows a state in which the needle shaft 10, outer sheath 20 and guide tube 30 are mounted to a soft or rigid endoscope using the manipulating section 60 according to this embodiment. As illustrated, the sockets 19, 29 and 39 at the basal ends of the needle shaft 10, outer sheath 20 and guide tube 30 are adapted to be directly received by the holders 81, 78 and 103, respectively. The holders 81, 78 and 103 are movably fixed to the frame plate 71 with the lock nuts 83, 79 and 102 threaded to the projecting screw rods of the holders 81, 78 and 103. In addition, the slot 72 in this embodiment is longer in length than the slot 72 in the previous embodiment so as to additionally provide a movable range for the socket 39.

Accordingly, in this embodiment, the reciprocal movement manipulating section 70 of the manipulating section 60 permits the guide tube 30 to be moved back and forth. That is, if the guide tube lock nut 102 is tightened, the guide tube holder 103 holding the socket 39 of the guide tube 30 is fixed to the frame plate 71, and if the guide tube lock nut 120 is loosened, the guide tube holder 103 becomes free to move back and forth along the slot 72.

Given this design, each of the socket 19, 29 and 39 can be moved along the arrow A direction along the slot 72 independently of one another, and can be fixed at any arbitrary position to the frame plate 71, with the exception of changing the order of the arrangement of these sockets 19, 29 and 39.

More specifically, the manipulating section 60 permits various operation, such as moving the needle shaft 10 back and forth with the outer sheath 20 fixed with respect to the endoscope 90 after the guide tube 30 is fixed so that the distal end of the guide tube 30 is slightly projected from or retracted into the distal end portion of the insertion portion 92 of the endoscope 90, moving the outer sheath 20 back and forth with the needle shaft 10 fixed with respect to the endoscope 90, fixing both the outer sheath 20 and needle shaft 10, etc., as desired, thereby enabling each collection of the tissue specimen 101 with a simple way.

Figure 24:
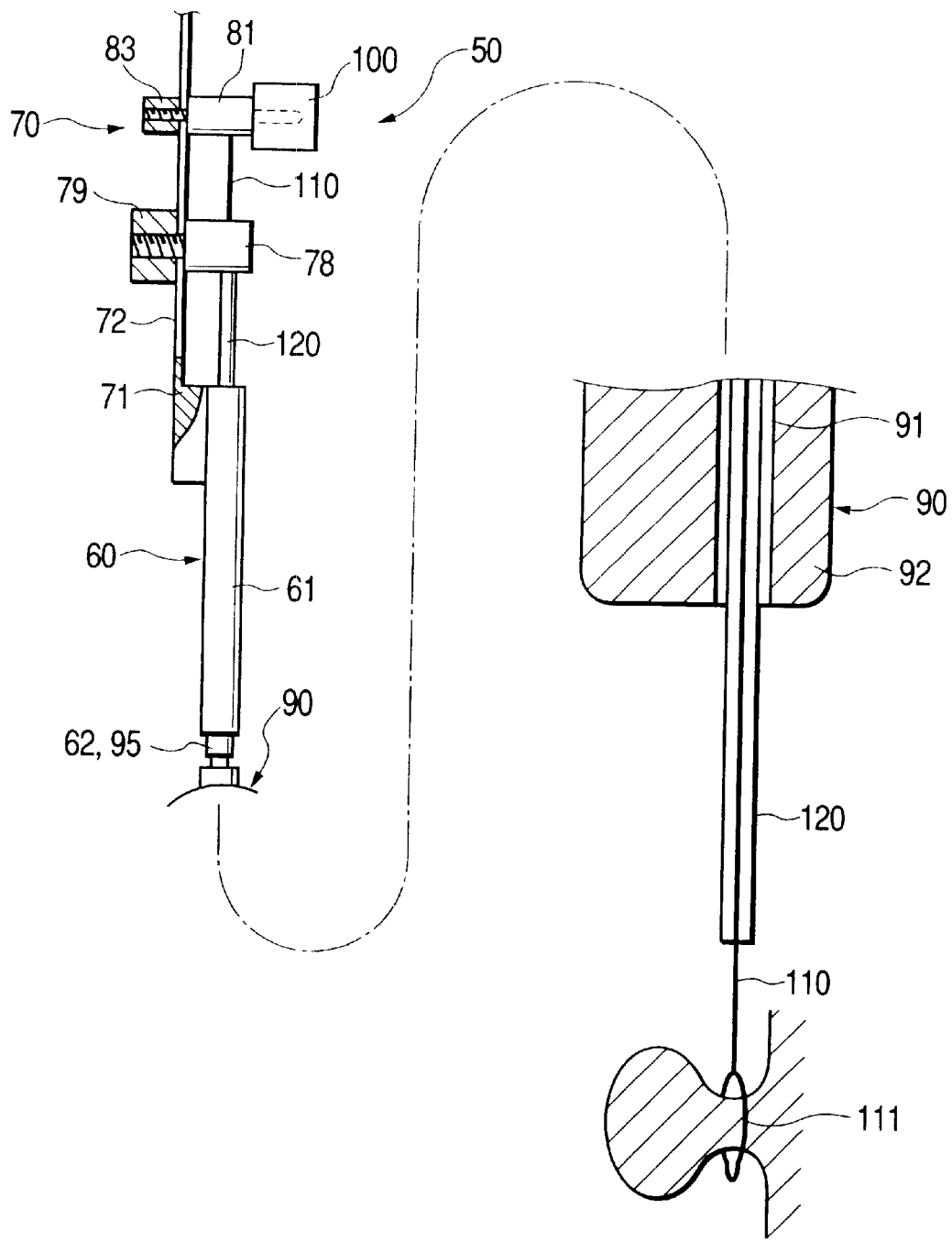
FIG. 24 schematically showing how an endoscopic snare is set in the endoscope.

The present invention is applicable to not only a Menghini tissue collecting needle but also other various endoscopic treatment instruments, such as an endoscopic forceps, an endoscopic snare, etc. FIG. 24 shows an example in which the present invention is applied to endoscopic snare for incising a polyp, or the like. The endoscopic snare includes an outer sheath 120 and an manipulating wire 110 that is provided with a snare loop at its distal end for tightening a polyp and that is inserted into and passed through the outer sheath to be movable back and forth. The endoscopic snare in this example is not provided with the guide tube 30. The basal end of the manipulating wire is fixedly received by the holder 81, and the basal end of the outer sheath 120 is fixedly received by the holder 78. In addition, reference numeral 100 denotes a connection terminal, provided to the holder 81, for electric connection of a high-frequency power supply cable to the manipulating wire 110. Other components are the same as those described with reference to the previous embodiments, and thus denoted by the same reference numerals.

What is claimed is:

1. A manipulating section for an endoscopic treatment instrument including a hollow, first member and a second member inserted into and movable relative to the first hollow member, the manipulating section comprising:
    a first plate;
    a first holding member holding an end of the first hollow member, the first holding member being movable along the plate, and selectively fixed with respect to the plate;
    a second holding member holding an end of the second member, the second holding member being movable along the plate, and selectively fixed with respect to the plate.

2. The manipulating section according to claim 1, further comprising:
    a coupling section connecting the plate to a socket of an endoscope, the socket being located at an inlet of a treatment instrument insertion channel of the endoscope.

3. The manipulating section according to claim 2, wherein the first holding member is located between the coupling section and the second holding member.

4. The manipulating section according to claim 1, further comprising:
    a second plate movable along and selectively fixed with respect to the first plate;
    wherein the first holding member is movable along the second plate and selectively fixed onto the second plate, and
    the second holding member is fixed onto the second plate.

5. The manipulating section according to claim 1, further comprising:
    a second plate through which the first holding member is movable along the first plate, and selectively fixed with respect to the first plate.

6. The manipulating section according to claim 1, wherein the treatment instrument further includes a hollow, third member, the second member is inserted into and movable relative to the third member, and an end of the third member is fixedly coupled with respect to the first plate.

7. The manipulating section according to claim 5, wherein the first member includes an outer sheath, the second member includes a needle shaft, and the third member includes a guide tube.

8. The manipulating section according to claim 1, wherein the second member is hollow, and the treatment instrument further includes a third member inserted into and movable relative to the hollow, second member, the manipulating section further comprising:
    a third holding member holding an end of the third member, the third holding member being movable along the first plate, and selectively fixed with respect to the first plate.

9. The manipulating section according to claim 8, wherein the first member includes a guide tube, the second member includes an outer sheath, and the third member includes a needle shaft.

10. The manipulating section according to claim 1, wherein the first member includes an outer sheath, and the second member includes a snare wire.

11. A manipulating section for an endoscopic tissue collecting instrument having a needle shaft with a needle tip formed at a distal end thereof, and an outer sheath fitted over the needle shaft to be capable of moving back and forth along a longitudinal axis, one of the needle shaft and the outer sheath having a tissue retaining recess formed in a lateral side of an area close to the distal end and the other of the outer sheath and the needle shaft having a blade formed at the distal end to cut off a tissue retained in the recess, the manipulating section being designed such that:

the manipulating section can be fixed to or disengaged from an entrance of a treatment instrument insertion channel in an endoscope;

a basal end portion of the needle shaft and a basal end portion of the outer sheath can be moved back and forth in unison along the longitudinal axis or fixed; and one of the basal end portion of the needle shaft and the basal end portion of the outer sheath is adapted to be capable of moving along the longitudinal axis or being fixed relative to the other of the basal end portion of the outer sheath and the basal end portion of the needle shaft.

12. The manipulating section according to claim 11, wherein a slider plate is provided in such a way that the one of the basal end portion of the needle shaft and the basal end portion of the outer sheath is engaged with the slider plate movably to be capable of moving along the longitudinal axis, and the other of the basal end portion of the outer sheath and the basal end portion of the needle shaft is fixed to the slider plate, and the slider plate is capable of moving back and forth or being fixed relative to a frame of the manipulating section.

13. The manipulating section according to claim 11, wherein the needle shaft and the outer sheath each have flexibility.

14. The manipulating section according to claim 11, wherein the needle shaft and the outer sheath are passed through a guide tube over the entire length thereof, and a basal end of the guide tube is brought into engagement in the manipulating section.

15. A manipulating section for manipulating, from an operator side, an endoscopic treatment instrument having an outer sheath inserted into and passed through a treatment instrument insertion channel in an endoscope and adapted to be manipulated, from the operator side, to be moved back and forth along a longitudinal axis, and an elongating member disposed within and passed through the outer sheath, and adapted to be manipulated, from the operator side, to be moved back and forth along the longitudinal axis, the manipulating section comprising:

a frame plate adapted to be fixed to or disengaged from an entrance of the treatment instrument insertion channel in the endoscope;

an outer sheath lock nut by which a basal end portion of the outer sheath can be moved back and forth on an elongation of an axis of the entrance of the treatment instrument insertion channel along the frame plate or fixed; and an elongating member lock nut by which a basal end portion of the elongating member can be moved back and forth on the elongation of the axis of the entrance of the treatment instrument insertion channel along the frame plate or fixed.

16. The manipulating section according to claim 15, wherein a guide tube is provided, which is inserted into and passed through the treatment instrument insertion channel in the endoscope, the outer sheath being inserted into and passed through the guide tube.

17. The manipulating section according to claim 16, further comprising:

a guide tube lock nut by which a basal end portion of the guide tube can be moved back and forth on the elongation of the axis of the entrance of the treatment instrument insertion channel along the frame plate or fixed.

* * * * *